United States Patent
Dalbert

(10) Patent No.: US 11,234,884 B2
(45) Date of Patent: Feb. 1, 2022

(54) MEDICAL APPARATUS AND METHOD FOR OPERATING THE MEDICAL APPARATUS

(71) Applicant: TRUMPF MEDIZIN SYSTEME GMBH + CO. KG, Saalfeld (DE)

(72) Inventor: Heinz-Hermann Dalbert, Bruckmuehl (DE)

(73) Assignee: TRUMPF MEDIZIN SYSTEME GMBH +CO. KG, Saalfeld (DE)

( * ) Notice: Subject to any disclaimer, the term of this patent is extended or adjusted under 35 U.S.C. 154(b) by 55 days.

(21) Appl. No.: 16/686,892

(22) Filed: Nov. 18, 2019

(65) Prior Publication Data
US 2020/0155403 A1 May 21, 2020

(30) Foreign Application Priority Data
Nov. 20, 2018 (EP) ..................................... 18207337

(51) Int. Cl.
*H05G 1/02* (2006.01)
*A61G 13/10* (2006.01)
(Continued)

(52) U.S. Cl.
CPC ............ *A61G 13/10* (2013.01); *A61B 6/4452* (2013.01); *A61B 6/4458* (2013.01);
(Continued)

(58) Field of Classification Search
CPC ........ A61B 2090/367; A61B 2090/376; A61B 6/0487; A61B 6/4452; A61B 6/4458; A61B 6/5229; A61B 6/5235; A61B 6/032; A61B 6/025; A61B 6/027; A61B 6/4014; A61B 6/4233; A61B 6/4435; A61B 6/4405; A61B 6/4476; A61B 6/547; A61B 6/583; A61B 6/4441; A61B 6/4464; A61B 6/503; A61B 6/487; A61B 6/12; A61B 6/504; A61B 6/0407; A61B 6/40; A61B 6/4085; A61B 6/463; A61B 6/465; A61B 6/467; A61B 6/481; A61B 6/5205; A61B 6/5211; A61B 6/5223; A61B 6/102; A61B 6/461; A61B 6/03; A61B 6/5294; A61B 6/0435; A61B 6/4035; A61B 6/405; A61B 6/4078; A61B 6/0478; A61B 6/14; A61B 6/04; A61B 6/542; A61B 6/544; A61G 13/10; A61G 2210/50; G01N 23/046; G01N 23/04; G01N 33/573; G01N 2223/308; G01N 2223/639;
(Continued)

(56) References Cited

U.S. PATENT DOCUMENTS 9,125,611 B2 * 9/2015 Eaves .................. A61B 6/4441
2004/0234042 A1 * 11/2004 Ergun .................... A61B 6/405
378/209

(Continued)

FOREIGN PATENT DOCUMENTS

WO  WO2017/210500  12/2017

*Primary Examiner* — Irakli Kiknadze
(74) *Attorney, Agent, or Firm* — Barnes & Thornburg LLP

(57) ABSTRACT

A medical apparatus is provided. The medical apparatus comprises an operating table provided with a base and a tabletop for supporting a patient, an x-ray detector attached to the operating table, and at least one x-ray source configured to be attached to the operating table in a manner so as to be movable with respect to the operating table.

20 Claims, 2 Drawing Sheets

(51) Int. Cl.
*A61B 6/00* (2006.01)
*G01N 23/046* (2018.01)
*A61B 90/00* (2016.01)

(52) U.S. Cl.
CPC ...... *G01N 23/046* (2013.01); *A61B 2090/367* (2016.02); *A61B 2090/376* (2016.02); *A61G 2210/50* (2013.01)

(58) Field of Classification Search
CPC ........... G01N 2223/419; G01N 23/044; G01N 2223/1016; G01N 2223/301; G01N 2223/423; G01N 2223/628; G01N 2223/64; G01N 23/043; G01N 29/28; G06T 11/006; G06T 2200/04; G06T 7/11; G06T 11/008; G06T 2207/10024; G06T 2207/10028; G06T 2207/10081; G06T 2207/30004; G06T 7/30; G06T 2207/10016; G06T 2207/10121; G06T 2207/30048; G06T 2207/30101; G06T 2210/41; G06T 3/0068; G06T 7/0012; G06T 7/337; G06T 7/00; G06T 7/005; G06T 1/16; G06T 1/1644; G06T 5/50; G06T 11/203; G06T 2207/10116; G06T 5/002; G06T 11/20; G06T 15/08; G06T 19/00; G06T 2207/10004; G06T 2207/10088; A61N 2005/1061; A61N 5/1048; A61N 5/1049; A61N 5/1067; A61N 5/10; A61N 5/1039; A61N 5/1081; A61N 5/1082; A61N 2005/1062; A61N 2005/1092; A61N 5/1037; A61N 5/1042; A61N 5/1065; A61N 2005/1052; A61N 2005/1054; A61N 2005/1055; A61N 5/1036; A61N 5/1045; A61K 38/00; G21K 1/10; G21K 7/00; H01J 2235/068; H01J 35/065; H01J 35/186; G01V 5/0008; G01V 5/0066; G01V 5/0016; G01V 5/0025; H05G 1/02; H05G 1/08; H05G 1/04; H05G 1/06; H05G 1/085; H05G 1/10; H05G 1/12; H05G 1/14; H05G 1/265; H05G 1/32; H05G 1/54; H05G 1/56; H05G 1/60; G01T 7/00; G01T 7/005; G01T 1/16; G01T 1/1644; G01T 1/2985; G01T 1/1615; G01T 1/00; G01T 1/04
USPC .............. 378/19, 20, 68, 102, 195–198, 208
See application file for complete search history.

(56) References Cited

U.S. PATENT DOCUMENTS

| | | |
|---|---|---|
| 2007/0263768 A1* | 11/2007 | Ullberg ................ A61B 8/4416 378/63 |
| 2011/0058647 A1 | 3/2011 | Star-Lack et al. |
| 2013/0230137 A1 | 9/2013 | Keeve et al. |
| 2014/0294152 A1 | 10/2014 | Florent et al. |
| 2017/0200271 A1 | 7/2017 | Atria et al. |
| 2017/0347978 A1* | 12/2017 | Kuspert ................ A61B 6/4482 |

* cited by examiner

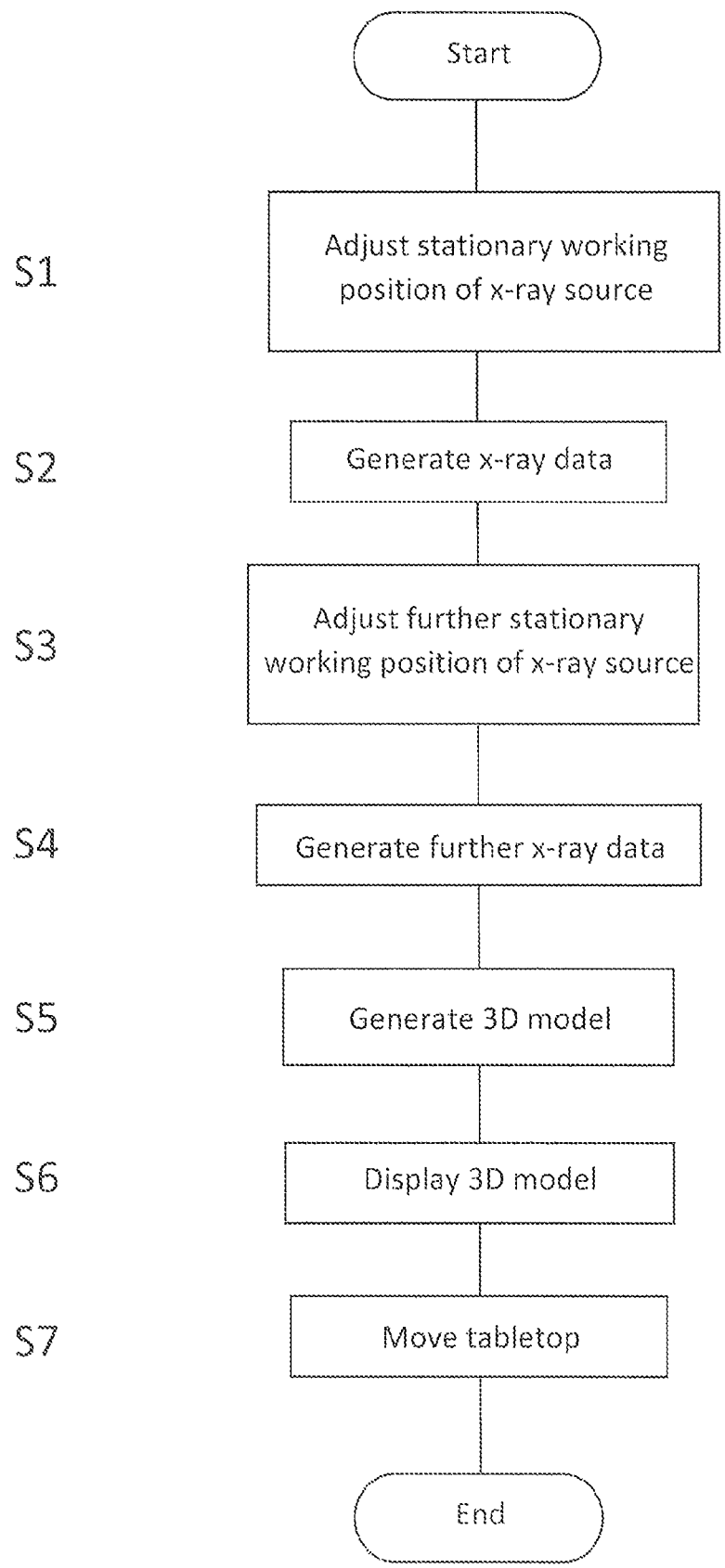

MEDICAL APPARATUS AND METHOD FOR OPERATING THE MEDICAL APPARATUS

CROSS-REFERENCE TO RELATED APPLICATIONS

This application claims the benefit of European Patent Application Serial No. 18207337.9, filed on Nov. 20, 2018, the entire disclosure of which is incorporated herein by reference in its entirety.

TECHNICAL FIELD

The disclosure relates to a medical apparatus and a method for operating the medical apparatus, in particular, to a medical apparatus and a method for operating the medical apparatus in the field of robotic surgery.

BACKGROUND

Typical existing x-ray imaging systems which are used in intraoperative diagnostic are imaging systems using a C-arm. At the ends of the C-arm, respectively an x-ray source and an x-ray detector are provided. The C-arm including the x-ray source and the x-ray detector is rotated 360 degrees around an object, i.e., around a patient, to generate a scan for a 3D image.

For the generation of the 3D image, the imaging system has to be moved from a parking position farther away from an operating table where the imaging system does not interfere the work process of the operation personnel to a position close to the operating table.

However, this is elaborate and causes concerns in regard to possible collisions with the patient, the operating table and further persons or objects.

Furthermore, a diameter of the C-arm has to be appropriate for the scaning procedure so that, as the case may be, a large diameter of the C-arm would be necessary. The use of the rotating C-arm can further be limited due to lines or hoses connected to the patient and, moreover, due to robotic arms used in robotic supported minimal invasive surgery.

Therefore, the object underlying the disclosure is to provide a medical apparatus which enables a simple and safe positioning of an x-ray device.

SUMMARY

The present disclosure includes one or more of the features recited in the appended claims and/or the following features which, alone or in any combination, may comprise patentable subject matter.

According to an aspect of the disclosure, a medical apparatus comprises an operating table provided with a base and a tabletop for supporting a patient, an x-ray detector attached to the operating table, and at least one x-ray source, configured to be attached to the operating table in a manner so as to be movable with respect to the operating table.

By the provision of the x-ray detector and the at least one x-ray source at the operating table, there is no need to move an x-ray device from a remote positon to the operating table. This avoids collisions on the way from a parking position to a working position. Furthermore, when the x-ray source is movable with respect to the operating table, a suitable working position of the x-ray source can be adjusted and an image of a requested portion of the patient can be generated without repositioning the patient.

Due to an attachment of the at least one x-ray source and the x-ray detector to the operating table, a defined relationship between them is possible, wherein, due to the movability, the at least one x-ray source can be removed from a working area of the operation personnel into a parking position when it is not used.

According to an implementation of the medical apparatus, the medical apparatus comprises at least one motion element to which the at least one x-ray source is attached, the motion element being provided with a drive and a controller configured to adjust various spatial positions of an x-ray source attached thereto in a direction having a vertical component.

In case that the medical apparatus is provided with the at least one motion element to which one of the at least one x-ray source is attached and which is provided with a drive and a controller, due to a flexibility of the motion element, various spatial positions of the x-ray source can be adjusted. Therefore, same spatial positions can exactly be taken up after a removal of the x-ray source during surgery, e.g., for monitoring results during or after the surgery. Due to the provision of the drive and of the controller, working positions of the x-ray source can be easily approached without any effort. When a motion in a direction having a vertical component is possible, the at least one x-ray source can easily be removed from the working range of a surgeon or of a surgical robot.

According to a further implementation of the medical apparatus, the tabletop has a lying surface, the motion element of the at least one x-ray source is configured to move the at least one x-ray source into a position above a plane comprising the lying surface and being parallel to the lying surface and laterally of the patient, and the x-ray detector is attached below the lying surface of the tabletop.

When the x-ray source is moved into a position above the plane comprising the lying surface and the x-ray detector is attached to the operating table below the lying surface, there is no need for removing the x-ray detector during a surgical intervention and the x-ray source can be moved into its working position so that the patient or a portion of the patient is located between the x-ray source and the x-ray detector. Since the x-ray source is moved laterally of the patient, instruments, such as trocars, upwardly protruding from the patient's body, in particular, when used by a surgical robot, do not hinder the capture of an x-ray image.

In a further implementation of the medical apparatus, the motion element is configured to additionally move the at least one x-ray source in a direction having a component in a direction along a longitudinal axis of the operating table.

Due to the option to move the x-ray source in a direction along the longitudinal axis of the operating table, x-ray images of requested portions along the body of the patient can be captured.

According to a further implementation of the medical apparatus, the motion element is attached to the base.

When the motion element and, therefore, the x-ray source is attached to the base, removal of the tabletop is possible without being hindered by the x-ray source. Therefore, the patient supported by the tabletop in an appropriate posture for the surgery can be moved into an operating theater before the surgical intervention and, after the surgical intervention, the patient can be moved out of the operating theater supported by the tabletop.

According to a further implementation of the medical apparatus, the tabletop is configured to be displaceable and to be tiltable, and the medical apparatus is configured such that the at least one x-ray source follows a motion of the tabletop.

Since the x-ray source follows the motion of the tabletop, changes, e.g., of positions of organs of a patient, can be monitored during the motion in real time. In case of an attachment of the x-ray source to the tabletop, the x-ray source automatically follows the motion of the tabletop and, in case of the attachment to the base, the controller and the drive of the motion element are configured such that the x-ray source follows the tabletop.

In a further implementation of the medical apparatus, the operating table is configured to be a mobile operating table.

By the provision of the operating table as the mobile operating table, an enhanced flexibility in the operating theater is possible due to various possible positions of the entire operating table. Moreover, the already appropriately supported patient can be brought into and out of the operating theater without removing the tabletop from the base.

According to a further implementation of the medical apparatus, the x-ray detector is configured to be attached to or integrated in the tabletop such that it covers an entire face of the tabletop.

When the x-ray detector covers the entire face of the tabletop, the x-ray image of an arbitrary portion of the patient can be captured without repositioning the x-ray detector or the patient.

According to a further implementation, the medical apparatus comprises two contralateral x-ray sources and a computer configured to generate a 3D model of at least a portion of the patient from the x-rays emitted by the two x-ray sources and detected by the x-ray detector.

By this configuration, 3D models can be generated in real time and they can be displayed and/or stored so that, in particular, in the case of minimal invasive surgery, a success of the surgery can be immediately approved additionally to images from an endoscopic camera.

In a further implementation, the medical apparatus comprises a monitor, wherein the computer is configured to display the 3D model matched to a live image or to a previously stored image or 3D model on the monitor.

When an illustration of the current 3D model is matched to a live image, a further progress of the surgery, e.g., when removing a tumor, can currently be planned since tissue to be removed can be determined from the x-ray image and it can be evaluated in the live image. By matching the 3D model of the actual portion of the patient with an image of a retrieved previously stored 3D model, e.g., success of a treatment can be monitored.

According to a further aspect of the disclosure, a method for operating a medical apparatus according to any preceding claim comprises the steps: adjusting a stationary working position of the at least one x-ray source such that at least a portion of the patient is located between the x-ray source and the x-ray detector, and generating x-ray data of the portion of the patient.

Located between the x-ray source and the x-ray detector means that the portion of the patient is located therebetween such that x-rays emitted from the x-ray source are passed through the portion of the patient and received by the x-ray detector.

By the positioning of the at least one x-ray source movably attached to the operating table, there is no need to move an x-ray device from a remote position to the operating table which avoids collisions on a way from a parking position to a working position. Furthermore, there is no need for repositioning the patient for capturing the image of the requested portion of the patient.

In an implementation of the method, the stationary working position is adjusted by moving the at least one x-ray source from a position below the tabletop.

When the working position is adjusted by this motion, the x-ray source is in a parking position below the tabletop where it does not interfere the working range of the operation personnel or of a surgical robot.

According to an implementation, the method includes the further steps of adjusting a further stationary working position different from the working position of the at least one x-ray source such that the same portion of the patient is located between the x-ray source and the x-ray detector, and generating further x-ray data of the same portion of the patient.

By this step, generation of the 3D model with merely one x-ray source is possible so that the investment costs are reduced.

According to a further implementation, the method includes the further step of generating a 3D model from data generated by the x-ray detector from x-rays emitted by two contralateral x-ray sources or from x-rays subsequently emitted by the at least one x-ray source at different stationary working positions.

Due to this further step, 3D models can be generated in real time and they can be displayed and/or stored so that, in particular, in the case of minimal invasive surgery, a success of the surgery can be immediately approved additionally to images from an endoscopic camera.

In a further implementation, the method includes the further step of displaying the 3D model matched to a live image or to a previously stored 3D model of the portion of the patient.

By this further step, a further progress of the surgery, e.g., when removing a tumor, can currently be planned since tissue to be removed can be determined from the x-ray image and it can be evaluated in the live image. By matching the 3D model of the actual portion of the patient to an image of a retrieved previously stored 3D model, e.g., progress of a treatment can be monitored.

According to a further implementation, the method includes the further step of moving the tabletop and simultaneously moving the at least one x-ray source such that x-ray data of a same portion of the patient are generated.

In this further step, the motion of the tabletop changes, e.g., positions of organs of a patient and due to the simultaneous motion of the x-ray source, the organs can be monitored in real time.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 2 shows a flowchart illustrating a method for operating the medical apparatus of FIG. 1.

DETAILED DESCRIPTION OF THE DRAWINGS

Figure 1:
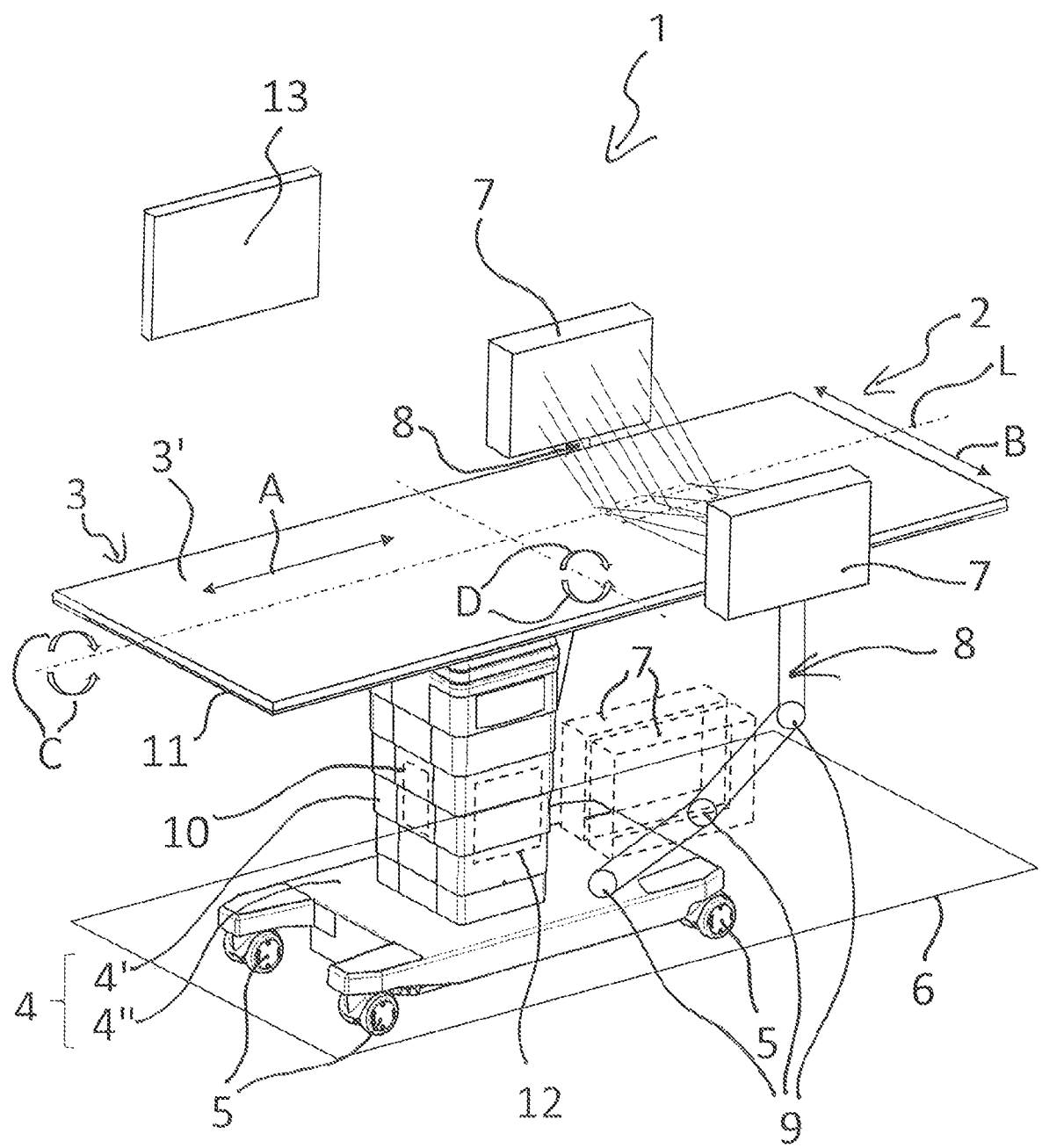
FIG. 1 shows a principle illustration of an embodiment of a medical apparatus according to the disclosure.

FIG. 1 shows a principle illustration of an embodiment of a medical apparatus 1 according to the disclosure.

The medical apparatus 1 comprises an operating table 2. The operating table 2 is provided with a tabletop 3 for supporting a patient (not shown) and a base 4. The base 4 comprises a column 4' and a chassis 4". The chassis 4" is provided with castors 5 so that the operating table 2 is configured as a mobile operating table which is stationary during a surgical intervention. On an upper side, the tabletop 3 has a lying surface 3' for supporting the patient. In alternative embodiments, the operating table 2 is provided with a column 4' fixed to a floor 6 and with a tabletop 3 detachable from the column 4'.

The medical apparatus 1 further comprises two contralateral x-ray sources 7. The x-ray sources 7 are attached to the operating table 2 in a manner so as to be movable with respect to the operating table 2.

As shown in FIG. 1, the x-ray sources 7 depicted by solid lines are moved into positions above a plane comprising the lying surface 3' and lateral from the patient which are working positions of the x-ray sources 7. Even though a housing of the x-ray sources 7 may not be located in a position above the plane including the lying surface 3', an area of the x-ray sources 7 emitting x-rays is located in a position above this plane. The x-ray sources 7 depicted by dotted lines in FIG. 1 are shown in a parking position below the tabletop 3.

The medical apparatus 1 comprises motion elements 8 provided with drives 9. The motion elements 8 are attached to the base 4 of the operating table 2. In alternative embodiments, the x-ray sources 7 are attached to the operating table 2 by means of motion elements 8 which are to be manually operated and/or the motion elements 8 can be attached to another element of the operating table, e.g. to the tabletop 3.

The medical apparatus 1 furthermore comprises a controller 10. The motion elements 8 are provided with the drives 9 and the controller 10 which are configured to adjust various spatial positions of the x-ray sources 7 attached thereto in a direction having a vertical component. Thus, by the motion elements 8, which can, e.g., be configured as a flexible arm, the x-ray sources 7 are moved in an up and down direction and the respective stationary working position is adjusted by moving the x-ray sources 7 from the position below the tabletop, namely, from the parking position. In an alternative embodiment, the x-ray sources 7 are moved into the parking position in a vertical direction. Therefore, in this alternative embodiment, the x-ray sources 7 can additionally be moved in a direction having a horizontal component, i.e., a component along a longitudinal axis L of the operating table 2.

In an alternative embodiment, the medical apparatus comprises merely one x-ray source 7 and, in another embodiment, the medical apparatus comprises several x-ray sources 7.

The apparatus further comprises an x-ray detector 11 attached to the operating table 2. In this embodiment, the x-ray detector 11 is attached to the tabletop 3 and it covers an entire face of the tabletop 3. Covering the entire face of the tabletop 3 means that, at the edges of the tabletop 3, there can be a section which is not covered by the x-ray detector 7. The section is to be set such that portions irradiated by x-rays of a patient lying on the tabletop 2 in usual positions can be detected by the x-ray detector 11. In particular, the x-ray detector 11 is attached below the lying surface 3' of the tabletop 3.

The x-ray detector 11 is a flatbed detector formed in layers. An upper layer is formed as a scintillator comprising needle crystal of CsI (cesium iodide) and a lower layer is formed by a TFT sensor panel provided with photodiodes.

In alternative embodiments, the x-ray detector does not cover the entire face of the tabletop 3 but merely sections of the tabletop 3 relevant for specific kinds of surgery, e.g. abdominal surgery, the x-ray detector 3 forms the lying surface 3', the x-ray detector 11 has another structure or the x-ray detector 3 is attached to another component of the operating table 2.

The tabletop 3 is displaceable and tiltable. In particular, the tabletop 3 can be displaced in a direction depicted by an arrow A which is parallel to the lying surface 3' and has a component in the longitudinal axis L of the operating table 2, and in a direction depicted by an arrow B which is parallel to the lying surface 3' and has a component perpendicular to the longitudinal axis L of the operating table 2. The tabletop 3 is tiltable around an axis depicted by arrows C which is parallel to the direction depicted by the arrow A, and around an axis depicted by arrows D which is parallel to the direction depicted by the arrow B. The tabletop 3 is also tiltable around an isocenter located above the tabletop 3. In alternative embodiments, the tabletop 3 is not provided with all these kinds of maneuverability but only has some of them or the tabletop 3 is rigidly attached to the base 4.

The controller 10 is configured such that the x-ray sources 7 can follow a motion of the tabletop 3. The controller 10 is integrated in an operating table controller controlling the motions of the tabletop 3. In alternative embodiments, the controller 10 is a separate controller integrated in the operating table 2 or separately provided. Moreover, alternatively, the controller 10 is not configured such that the x-ray sources follow the motion of the tabletop 3.

The medical apparatus 1 is further equipped with a computer 12. The computer 12 generates a 3D model of at least a portion of the patient from the x-rays emitted by the x-ray sources 7 and detected by the x-ray detector 11. The medical apparatus 1 is further provided with a monitor 13. The computer 12 displays the 3D model on the monitor 13. In particular the computer 12 displays the 3D model matched to a live image or to a previously stored image or 3D model. In some embodiments, the monitor 13 is integrated in an operation console of a surgical robot, or it is not configured to match the 3D model with illustrations of other data, or it is omitted and the 3D data are merely stored.

Finally, a system comprising trocars or instruments provided with targets, such as reflecting stars, and with the medical apparatus is provided. The trocars or instruments are inserted into a patient's body and they are used for focusing the x-ray sources 7 to the isocenter or to a point of interest.

FIG. 2 shows a flowchart illustrating a method for operating the medical apparatus 1 of FIG. 1.

In use, in step S1, stationary working positions of the two contralateral x-ray sources 7 are adjusted such that at least a portion of the patient is located between the x-ray sources 7 and the x-ray detector 11. In particular, positions of the x-ray sources 7 are adjusted such that the portion of the patient to be examined is located in the x-rays emitted by the x-ray sources 7 and received by the x-ray detector 11. The stationary working position is adjusted by moving the x-ray sources 7 from the position below the tabletop 3. In an alternative embodiment, the parking positions of the x-ray sources 7 are located at another place, e.g. at a leg-side end of the operating table 2 such that the x-ray sources are moved into their working positions by a horizontal motion.

In step S2, x-ray data of the portion of the patient are generated.

In step S3, in the case that merely one x-ray source 7 is provided or used, a further stationary working position of the one x-ray source 7 is adjusted such that the same portion of the patient is located between the one x-ray source 7 and the x-ray detector 11 and, in S4, further x-ray data of the same portion of the patient are generated. Alternatively, steps S3 and S4 can be omitted or, in the case that several x-ray sources 7 are provided, they can be executed with one or several x-ray sources 7 for enhancing a quality of the x-ray data.

Subsequently, in step S5, a 3D model from data generated by the x-ray detector 11 from the x-rays emitted by two contralateral x-ray sources 7 or from x-rays subsequently emitted by the at least one x-ray source 7 at different stationary working positions is generated. In case that, e.g., merely a single x-ray image is captured, this step is alternatively omitted.

In step S6, the 3D model is displayed on a suitable device, such as the monitor 13. The 3D model is matched to a live image or to a previously stored 3D model of the portion of the patient. Alternatively, displaying of the live image or of the previously stored 3D model of the portion of the patient is omitted and merely the current x-ray image is displayed.

In step S7, the tabletop 3 is moved and simultaneously the two x-ray sources 7 are moved such that x-ray data of a same portion of the patient are generated. Alternatively, moving of the tabletop 3 is not envisaged.

Finally, at any suitable time, the trocars or instruments provided with the targets are inserted into the patient's body such that they indicate the isocenter or the point of interest. Subsequently, the x-ray sources 7 are focused to one of the targets.

While embodiments of the invention have been illustrated and described in detail in the drawings and the foregoing description, such illustration and description are to be considered illustrative or exemplary and not restrictive. The inventive aspects of the disclosure are not limited to the disclosed embodiments. From reading the present disclosure, other modifications will be apparent to a person skilled in the art. Such modifications may involve other features, which are already known in the art and may be used instead of or in addition to features already described herein. In the claims, the word "comprising" does not exclude other elements or steps, and the indefinite article "a" or "an" does not exclude a plurality. Although this disclosure refers to specific embodiments, it will be understood by those skilled in the art that various changes in form and detail may be made without departing from the subject matter set forth in the accompanying claims.

The invention claimed is:

1. A medical apparatus comprising
    an operating table provided with a base and a tabletop for supporting a patient, the tabletop being movable relative to the base,
    an x-ray detector attached to the operating table, and
    at least one x-ray source, the x-ray source attachable to a component of the operating table to be movable with respect to the base of the operating table and independently of the tabletop of the operating table,
    wherein the component of the operating table comprises at least one motion element to which the at least one x-ray source is attached, the at least one motion element being provided with a drive and a controller configured to adjust various spatial positions of the x-ray source attached thereto in a direction having a vertical component,
    wherein the motion element is attached to the base of the operating table.

2. The medical apparatus of claim 1, wherein
    the tabletop has a lying surface,
    the motion element moves the at least one x-ray source into a position above a plane comprising the lying surface and being parallel to the lying surface and laterally from the patient, and
    the x-ray detector is attached below the lying surface of the tabletop.

3. The medical apparatus of claim 1, wherein the motion element is configured to additionally move the at least one x-ray source in a direction having a component in a direction (A) along a longitudinal axis (L) of the operating table.

4. The medical apparatus of claim 1, wherein the tabletop is configured to be displaceable and to be tiltable, and the medical apparatus is configured such that the at least one x-ray source follows a motion of the tabletop.

5. The medical apparatus of claim 4, wherein the controller and the drive of the motion element are configured such that the motion of the at least one x-ray source relative to the base follows the motion of the tabletop relative to the base.

6. The medical apparatus of claim 1, wherein the operating table is configured to be a mobile operating table.

7. The medical apparatus of claim 1, wherein the x-ray detector is configured to be positioned such that it covers an entire face of the tabletop.

8. The medical apparatus of claim 1, wherein the medical apparatus comprises two contralateral x-ray sources, and a computer configured to generate a 3D model of at least a portion of the patient from the x-rays emitted by the two contralateral x-ray sources and detected by the x-ray detector.

9. The medical apparatus of claim 8, further comprising a monitor, wherein the computer is configured to display the 3D model matched to a live image or to a previously stored image or 3D model on the monitor.

10. A method for operating a medical apparatus according to claim 1, comprising the steps:
    adjusting a stationary working position of the at least one x-ray source by the at least one motion element attached to the base of the operating table such that at least a portion of the patient is located between the x-ray source and the x-ray detector; and
    generating x-ray data of the portion of the patient.

11. The method of claim 10, wherein the stationary working position is adjusted by moving the at least one x-ray source from a position below the tabletop.

12. The method of claim 11 including the further steps:
    adjusting a further stationary working position different from the working position of the at least one x-ray source such that the same portion of the patient is located between the x-ray source and the x-ray detector, and
    generating further x-ray data of the same portion of the patient.

13. The method of claim 12, including the further step:
    generating a 3D model from data generated by the x-ray detector from x-rays emitted by two contralateral x-ray sources or from x-rays subsequently emitted by the at least one x-ray source at different stationary working positions.

14. The method of claim 13, including the further step:
    displaying the 3D model matched to a live image or to a previously stored 3D model of the portion of the patient.

15. The method of claim 14, including the further step:
moving the tabletop and simultaneously moving the at least one x-ray source such that x-ray data of a same portion of the patient are generated.

16. The method of claim 11, including the further step:
generating a 3D model from data generated by the x-ray detector from x-rays emitted by two contralateral x-ray sources or from x-rays subsequently emitted by the at least one x-ray source at different stationary working positions.

17. The method of claim 11, including the further step:
displaying the 3D model matched to a live image or to a previously stored 3D model of the portion of the patient.

18. The method of claim 11, including the further step:
moving the tabletop and simultaneously moving the at least one x-ray source such that x-ray data of a same portion of the patient are generated.

19. The method of claim 18, wherein the controller and the drive of the motion element are configured such that the motion of the at least one x-ray source relative to the base follows the motion of the tabletop relative to the base.

20. The medical apparatus of claim 1, wherein the controller and the drive of the motion element are configured such that the motion of the at least one x-ray source follows the motion of the tabletop.

* * * * *